United States Patent [19]

Schwenner et al.

[11] Patent Number: 5,063,239
[45] Date of Patent: Nov. 5, 1991

[54] AMINO-ESTERS OF DIHYDROPYRIDINES USEFUL FOR IMPROVING CIRCULATION IN PATIENTS

[75] Inventors: Eckhard Schwenner, Wuppertal; Hartmut Stegelmeier, Hilden; Stanislav Kazda, Wuppertal; Andreas Knorr, Erkrath, all of Fed. Rep. of Germany

[73] Assignee: Bayer Aktiengesellschaft, Leverkusen, Fed. Rep. of Germany

[21] Appl. No.: 520,419

[22] Filed: May 8, 1990

Related U.S. Application Data

[62] Division of Ser. No. 317,313, Mar. 1, 1989, Pat. No. 4,950,676, which is a division of Ser. No. 18,652, Feb. 25, 1987, Pat. No. 4,861,782.

[30] Foreign Application Priority Data

Mar. 8, 1986 [DE] Fed. Rep. of Germany ....... 3607821

[51] Int. Cl.$^5$ .................. C07D 211/78; A61K 31/44
[52] U.S. Cl. .................... 514/357; 546/319; 546/321
[58] Field of Search ............ 546/319, 321, 270; 514/356, 358, 357

[56] References Cited

U.S. PATENT DOCUMENTS 4,861,782  8/1989  Schwenner et al. ............... 514/294
4,950,676  8/1990  Schwenner et al. ............... 514/338

OTHER PUBLICATIONS

Chem. Abstracts, vol. 110 (25), Abst. No. 110:231,401n, Jun. 19, 1989.

Primary Examiner—Alan L. Rotman
Attorney, Agent, or Firm—Sprugn, Horn, Kramer & Woods

[57] ABSTRACT

Circulation active compounds of the formula

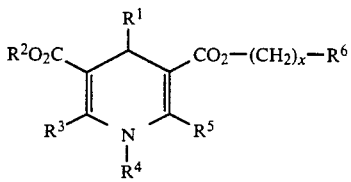

in which
R$^1$ is phenyl or heterocyclyl substituted by nitro, trifluoromethyl or other radicals,
R$^2$ is optionally substituted alkyl or other radical
R$^3$ and R$^5$ are hydrogen, methyl or other radicals,
R$^4$ is hydrogen or optionally substituted alkyl,
X is from 2 to 15, and
R$^6$ is

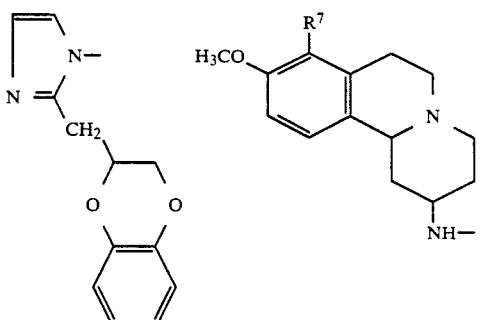

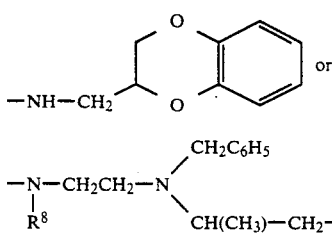

and physiologically acceptable salts thereof.

4 Claims, No Drawings

AMINO-ESTERS OF DIHYDROPYRIDINES USEFUL FOR IMPROVING CIRCULATION IN PATIENTS

This is a division of application Ser. No. 317,313, filed Mar. 1, 1989, now U.S. Pat. No. 4,950,676, which is a division of application Ser. No. 018,652, filed Feb. 25, 1987, now U.S. Pat. No. 4,861,782, issued Aug. 29, 1989.

The invention relates to amino-esters of dihydropyridines, processes for preparation and their use as medicaments, in particular as medicaments which influence the circulation.

It is known that diethyl 1,4-dihydro-2,6-dimethyl-4-phenyl-pyridine-3,5-dicarboxylate is obtained when ethyl 2-benzylideneacetoacetate is reacted with β-aminocrotonic acid ester or ethyl acetoacetate with ammonia [E. Knoevenagel, Ber. dtsch. Chem. Ges. 31, 743 (1898)].

It is also known that certain 1,4-dihydropyridines have interesting pharmacological properties [F. Bossert, W. Vater, Naturwissenschaften 58, 578 (1971)].

The present invention relates to new amino-ester dihydropyridines of the general formula (I)

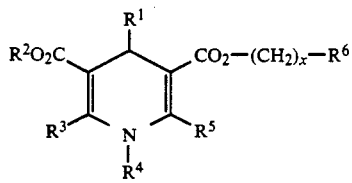

in which $R^1$ represents $C_6$–$C_{14}$-aryl, or represents heterocyclyl from the series comprising thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl, it being possible for the ring systems mentioned in each case to be substituted by one or two identical or different substituents from the group comprising phenyl, straight-chain or branched $C_1$–$C_4$-alkyl, $C_3$–$C_7$-cycloalkyl, $C_1$–$C_4$-alkoxy, $C_1$–$C_4$-alkylthio, tri-, tetra- or pentamethylene, dioxymethylene, dioxyethylene, halogen, trifluoromethyl, trifluoromethoxy, difluoromethoxy, tetrafluoroethoxy, nitro, cyano and azido, $R^2$ represents a straight-chain, branched or cyclic, saturated or unsaturated hydrocarbon radical which has up to 15 carbon atoms, is optionally interrupted in the chain by an oxygen atom or a sulphur atom and/or is optionally substituted by halogen, cyano, hydroxyl, $C_2$–$C_7$-acyloxy, nitro or nitrooxy or by a phenyl, phenoxy, phenylthio or phenylsulphonyl group, which is in turn optionally substituted by di-$C_1$–$C_2$-alkylamino, $C_1$–$C_4$-alkoxy, $C_1$–$C_4$-alkyl, halogen, trifluoromethyl or nitro, or by an α-, β- or γ-pyridyl group, or by an amino group, this amino group carrying two identical or different substituents from the group comprising $C_1$–$C_4$-alkyl, $C_1$–$C_6$-alkoxyalkyl, phenyl and benzyl, or the substituents optionally forming, with the nitrogen atom, a 5- to 7-membered ring which can contain, as a further hetero atom, an oxygen or sulphur atom or an N-phenyl or N-alkyl grouping, the alkyl group comprising one to three carbon atoms, $R^3$ and $R^5$ are identical or different and in each case represent hydrogen, a straight-chain, branched or cyclic alkyl radical with up to 8 carbon atoms or a phenyl or benzyl radical, or one of the substituents $R^3$ or $R^5$ represents an alkyl radical with up to 6 carbon atoms, which is substituted by acetoxy, benzoyloxy, $C_1$–$C_3$-alkoxy, $C_1$–$C_3$-dialkoxy, hydroxyl, amino, $C_1$–$C_6$-aminoalkoxy, phthalimido, $C_1$–$C_6$-phthalimidoalkoxy, $C_1$–$C_6$-piperidinoalkoxy, $C_1$–$C_6$-morpholinoalkoxy or N-phenyl-N'-piperazinoalkoxy with up to 6 carbon atoms, or represents formyl or nitrile, $R^4$ represents hydrogen, or represents a straight-chain or branched alkyl radical which has up to four carbon atoms, is optionally interrupted in the chain by an oxygen atom and/or is optionally substituted by a piperidino or morpholino radical, or represents phenyl or benzyl, X represents a number from 2 to 15 and $R^6$ represents a radical of the formula

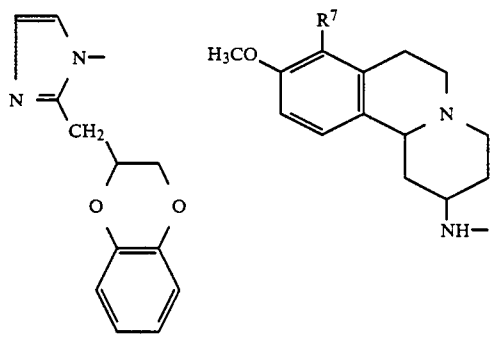

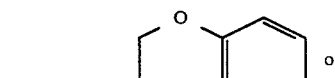

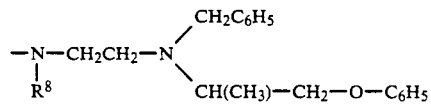

wherein $R^7$ represents hydrogen or methoxy and $R^8$ represents hydrogen, or represents straight-chain or branched $C_1$–$C_6$-alkyl, or represents the group of the formula

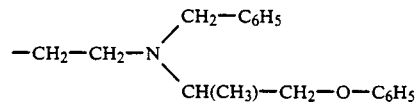

and physiologically acceptable salts thereof.

Preferred compounds of the formula (I) are those in which $R^1$ represents phenyl, thienyl, furyl, pyridyl, quinolyl or benzoxadiazolyl, the ring systems mentioned optionally being substituted by one or two identical or different substituents from the group comprising phenyl, $C_1$–$C_2$-alkyl, $C_1$–$C_2$-alkoxy, $C_1$–$C_2$-alkylthio, dioxymethylene, fluorine, chlorine, bromine and iodine, trifluoromethyl, trifluoromethoxy, difluoromethoxy, nitro and cyano, $R^2$ represents a straight-chain, branched or cyclic, saturated or unsaturated hydrocarbon radical which has up to 10 carbon atoms and is optionally interrupted in the chain by an oxygen atom and/or is optionally substituted by fluorine, chlorine, bromine, iodine, cyano, acetoxy or hydroxyl, or by a phenyl or phenoxy group which is optionally substituted by fluorine, chlorine, $C_1$-$C_2$-alkyl, $C_1$-$C_2$-alkyl, or trifluoromethyl, or by an α- or β- or γ-pyridyl group, or by a tertiary amino group, this amino group carrying two identical or different substituents from the group comprising $C_1$-$C_4$-alkyl, phenyl and benzyl, $R^3$ and $R^5$ are identical or different and in each case represent a straight-chain, branched or cyclic alkyl radical with up to 6 carbon atoms, or one of the substituents $R^3$ or $R^5$ represents an alkyl radical which has up to 4 carbon atoms and is substituted by acetoxy, methoxy, dimethoxy, hydroxyl, amino, phthalimido, aminoalkoxy or phthalimidoalkoxy with in each case up to 4 carbon atoms per alkoxy group, or represents formyl or cyano, $R^4$ represents hydrogen or represents a straight-chain or branched alkyl radical which has up to four carbon atoms, is optionally interrupted in the chain by an oxygen atom and/or is optionally substituted by a piperidino or morpholino radical or represents benzyl, X represents a number of 2 to 10, and $R^6$ represents a radical of the formula

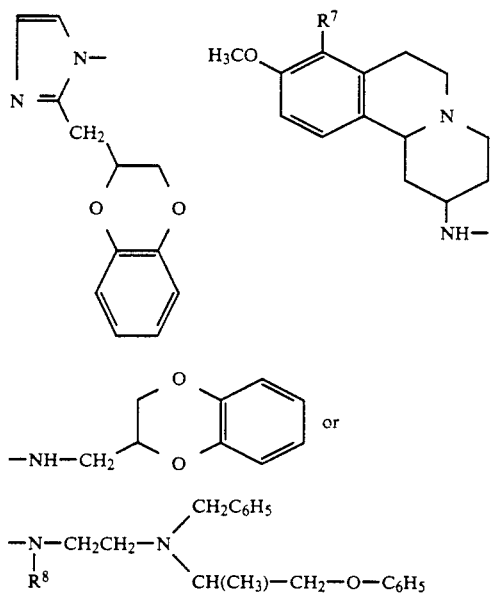

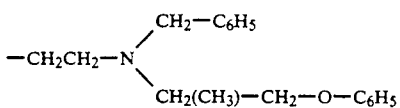

wherein $R^7$ represents hydrogen or methoxy and $R^8$ represents hydrogen, or represents straight-chain or branched $C_1$-$C_4$-alkyl, or represents the radical of the formula $$-CH_2CH_2-N\begin{matrix}CH_2-C_6H_5\\ CH_2(CH_3)-CH_2-O-C_6H_5\end{matrix}$$

and their physiologically acceptable salts.

Particularly preferred compounds of the general formula (I) are those in which $R^1$ represents phenyl, pyridyl or benzoxadiazolyl, the phenyl ring being substituted by 1 or 2 identical or different substituents from the group comprising chlorine, trifluoromethyl, nitro and cyano, $R^2$ represents a straight-chain or branched hydrocarbon radical which has up to 7 carbon atoms and is optionally interrupted in the chain by an oxygen atom and/or is optionally substituted by fluorine, cyano, phenyl or α-, β- or γ-pyridyl or by N-benzyl-N-methylamino, $R^3$ and $R^5$ represent methyl, $R^4$ represents hydrogen, X represents a number from 2 to 6 and $R^6$ represents a radical of the formula

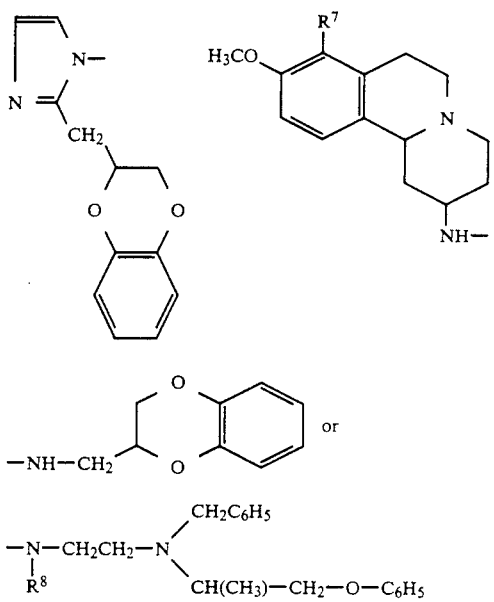

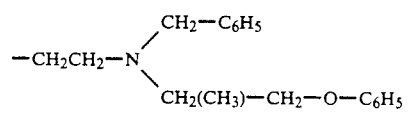

wherein $R^7$ represents hydrogen or methoxy and $R^8$ represents hydrogen, or represents straight-chain or branched $C_1$-$C_4$-alkyl, or represents the radical of the formula $$-CH_2CH_2-N\begin{matrix}CH_2-C_6H_5\\ CH_2(CH_3)-CH_2-O-C_6H_5\end{matrix}$$

and their physiologically acceptable salts.

Physiologically acceptable salts are salts of the compounds according to the invention with inorganic or organic acids. These include, preferably, inorganic acids, such as hydrogen halide acids, preferably HCl or HBr, sulphuric acid or phosphoric acid, or organic carboxylic acids or sulphonic acids, such as, for example, acetic acid, maleic acid, fumaric acid, malic acid, citric acid, tartaric acid, lactic acid, benzoic acid, methanesulphonic acid, ethanesulphonic acid, benzenesulphonic acid, naphthalenedisulphonic acid or totuenesulphonic acid.

The compounds according to the invention exist in stereoisomeric forms which either behave as mirror images (enantiomers) or do not behave as mirror images (diastereomers). The invention relates both to the antipodes and to the racemic forms as well as diastereomeric mixtures. The racemic forms, like the diastereomers, can be resolved into the stereoisomerically uniform constituents in a known manner (E. Eliel, Stereochemistry of Carbon Compounds McGraw Hill, 1962).

The amino-esters of dihydropyridines of the general formula (I) according to the invention are prepared by a process in which compounds of the general formula (II)

compounds of the general formula (I) according to the invention:

A) The compounds of the general formula (Ia) according to the invention

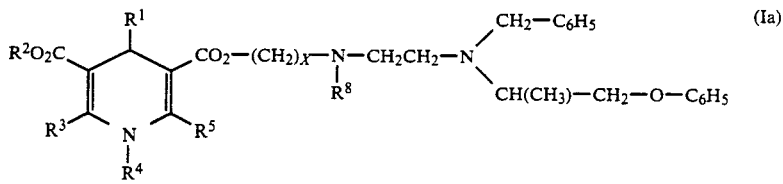

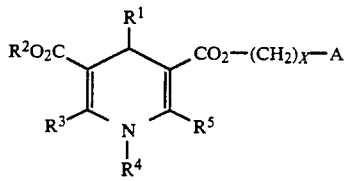

in which
$R^1$-$R^5$ and x have the abovementioned meaning and
A represents halogen or the radical $NHR^8$
wherein
$R^8$ has the abovementioned meaning
are reacted with compounds of the formula (III)

B—$R^6$ (III)

in which
$R^6$ has the abovementioned meaning and
B represents a reactive radical from the group comprising halogen, carbonyl and a secondary amino group,
in inert organic solvents at temperatures from 0° to 200° C. and, if starting compounds of the formula (III) with reactive carbonyl groups are used, the resulting Schiff's bases are reduced by customary methods.

The following preferred embodiments of the process according to the invention may be mentioned as preferred process variants for certain substituents of the in which
$R^1$-$R^5$, $R^8$ and X have the meaning given,
are obtained by a process in which amino compounds of the general formula (IIa)

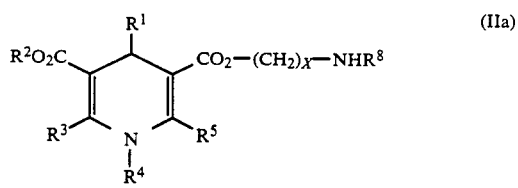

in which
$R^1$-$R^5$, X and $R^8$ have the meaning given,
are reacted with halogen compounds of the general formula (IIIa)

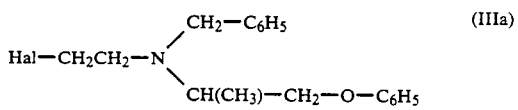

in which
Hal represents fluorine, chlorine, bromine or iodine, preferably chlorine or bromine,
in inert organic solvents, if appropriate in the presence of a base, if appropriate the products are then alkylated, and if appropriate the physiologically acceptable salts are prepared with acids.

Depending on the nature of the starting compounds used, the process according to the invention can be illustrated by the following equation:

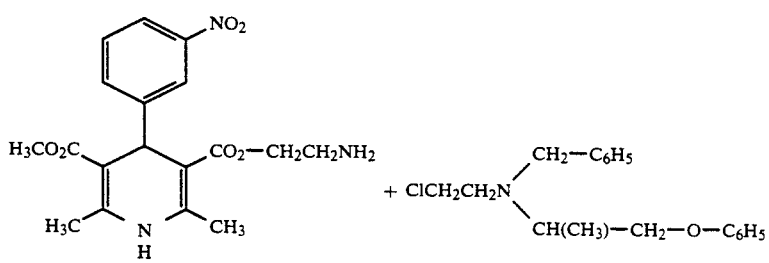

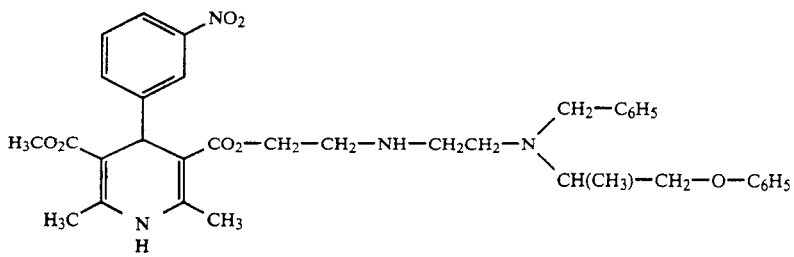

The amino compounds (IIa) employed as starting substances are known or can be prepared by known methods [U.S. Pat. No. 3,985,758; European Patent 151,006].

The halogen compounds of the formula (IIIa) used as starting substances are known or can be prepared by known methods [Biochem. Pharmacol., 30(12), 1685-92].

Solvents which can be used are the customary organic solvents which do not change under the reaction conditions. These include, preferably, alcohols, such as methanol, ethanol, propanol and isopropanol, ethers, such as diethyl ether, dioxane or tetrahydrofuran, dimethylformamide, dimethylsulphoxide, acetonitrile, ethyl acetate, hexamethylphosphoric acid triamide, pyridine, picoline, N-methylpiperidine and hydrocarbons, such as benzene, toluene or xylene. Mixtures of the solvents mentioned can likewise be employed.

Suitable bases are the customary inorganic or organic bases. These include, preferably, alkali metal hydroxides, such as sodium or potassium hydroxide, alkali metal carbonates, such as sodium or potassium carbonates, alkali metal alcoholates, such as sodium or potassium methanolate or sodium or potassium ethanolate, or organic amines, such as trialkylamines, for example triethylamine, pyridine, picoline or N-methylpiperidine, or amides, such as sodium amide or lithium diisopropylamide, or metalorganyls, such as, for example, butyl-lithium or phenyllithium.

The reaction is in general carried out in a temperature range from 0° C. to 200° C., preferably from room temperature up to the boiling point of the particular solvent.

The reaction is in general carried out under normal pressure. However, it is also possible to carry out the reaction under increased or reduced pressure.

For the synthesis of the compounds of the formula (Ia) in which $R^8$ represents hydrogen or $C_1$-$C_6$-alkyl, the corresponding amino compounds of the formula (IIa) are preferably employed in molar to twice the molar amounts. For the synthesis of the compounds of the formula (Ia) in which $R^8$ represents the group of the formula

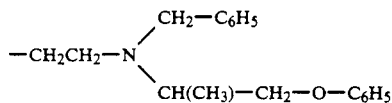

the corresponding halogen compound of the formula (IIIa) is preferably employed in twice to three times the molar amounts.

The base is employed in an amount of 1 to 100 mol, preferably 1 to 50 mol, per mol of amino compound.

If appropriate, subsequent alkylation is carried out by methods which are known per se, in inert solvents, such as alcohols, for example methanol, ethanol or n- or i-propanol, ethers, for example diethyl ether, dioxane or tetrahydrofuran, or halogenohydrocarbons, such as methylene chloride, chloroform or carbon tetrachloride, or hydrocarbons, such as benzene, toluene, xylene or hexane, with alkylating agents such as alkyl halides, preferably alkyl bromides or alkyl iodides, dialkyl sulphates or diazoalkanes, if appropriate with bases, such as NaOH, KOH or sodium or potassium hydroxide or organic bases, such as triethylamine or pyridine, as is described in detail, for example, in "Organikum", 11th edition, VFB Deutscher Verlag der Wissenschaften Berlin 1972, page 228.

B) The compounds of the general formula (Ib)

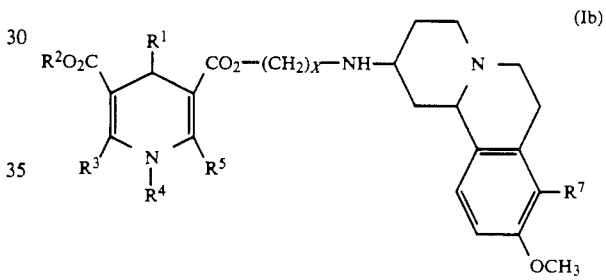

in which
$R^1$-$R^5$, $R^7$ and x have the meaning given,
are prepared by a process in which, in a first step, ketones of the formula (IIIb)

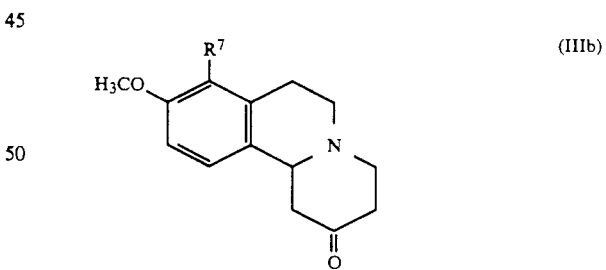

are reacted with amines of the formula (IIa) in which
$R^1$-$R^5$, $R^7$ and x have the meaning given and
$R^8$ represents hydrogen,
in an inert organic solvent, if appropriate in the presence of a catalyst, the Schiff's bases thus obtained are reduced in inert solvents in a second step and, if appropriate, the pharmacologically acceptable salts are then prepared with acids.

If 3-(2-aminoethyl) 5-methyl 1,4-dihydro-2,6-dimethyl-4-(3-nitrophenyl)-pyridine-3,5-dicarboxylate and 1,3,4,6,7,11b-hexahydro-8,9-dimethoxy-2-oxo-2H-benzo[a]-quinolizine of the formula (IIb) are used as starting substances, the synthesis of the compounds of the formula (Ib) according to the invention can be illustrated by the following equation:

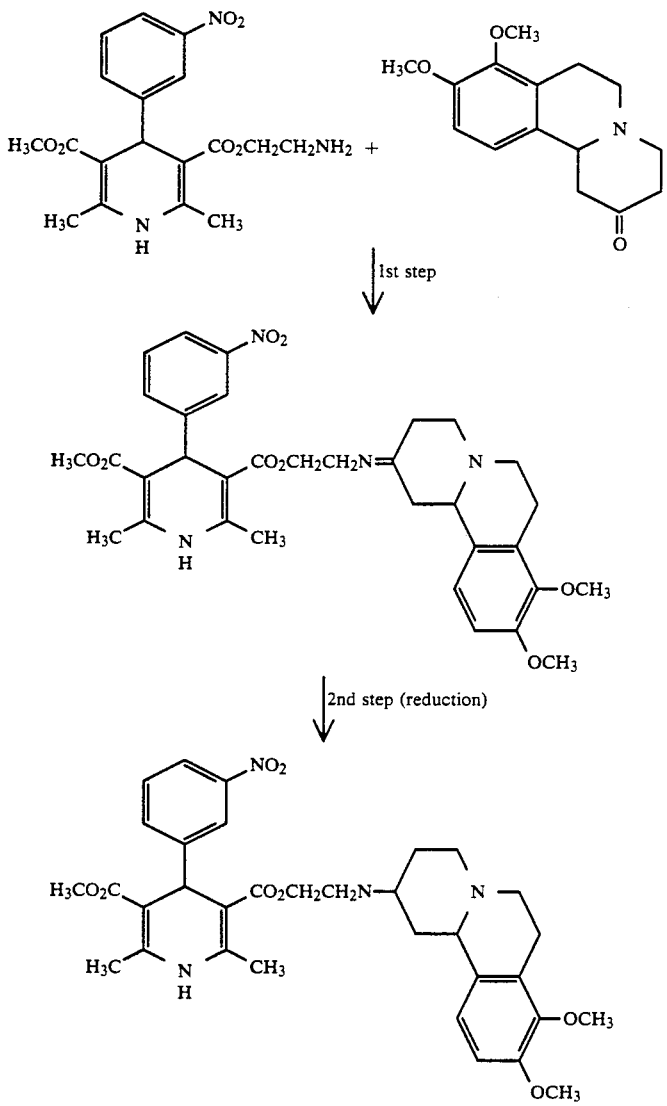

The ketones of the formula (IIIb) used as the starting material are new. They can be prepared by known methods, such as is described, for example, by D. Beke and C. Szantay in Chem. Ber. 95, 2132 (1962).

The compounds of the general formula (IIa) used as starting substances are known or can be prepared by known methods [U.S. Pat. No. 3,985,758; European Patent 151,006].

The preparation of the Schiff's bases in the first step is carried out in a manner which is known per se in inert organic solvents, if appropriate in the presence of a catalyst and if appropriate in the presence of a water-binding agent. The process according to the invention can be carried out in two steps, that is to say with isolation of the Schiff's bases. It is also possible to carry out the reaction as a one-pot process.

Suitable diluents here are the customary organic solvents which are not changed under the reaction conditions. These include, preferably, alcohols, such as methanol, ethanol, propanol or isopropanol, ethers, such as diethyl ether, dioxane or tetrahydrofuran, halogenohydrocarbons, such as, for example, methylene chloride, chloroform or carbon tetrachloride, dimethylformamide or aromatic hydrocarbons, such as, for example, benzene, toluene or xylene. It is also possible to use mixtures of the solvents mentioned.

Acids are in general used as catalysts. These include, preferably, inorganic acids, such as, for example, hydrochloric acid or sulphuric acid, or organic acids, such as, for example, methane-, ethane-, benzene- or toluenesulphonic acid, or acetic acid. It is also possible to use acetic acid as a mixture with acetic anhydride as a dehydrating agent. The water formed during the reaction can be removed, if appropriate as a mixture with the solvent used, during or after the reaction, for example by distillation, or by addition of water-binding agents, such as, for example, phosphorus pentoxide, or preferably by a molecular sieve.

The reaction is in general carried out at a temperature in the range from 0° C. to 150° C., preferably from 20° C. up to the boiling point of the particular solvent.

The reaction can be carried out under normal, increased or reduced pressure. It is in general carried out under normal pressure.

In carrying out the reaction, the starting substances are in general employed in a molar ratio of ketone IIIb to amine (IIa) of 0.5:2 to 1:2. Molar amounts of the reactants are preferably used.

The procedure for the preparation of the Schiff's bases from the ketone IIIb and amine (IIa) is not restricted to the variants described, but can also be carried out by other known methods, which are described, for example, in Houben-Weyl "Methoden der organischen Chemie" ("Methods of Organic Chemistry"), Volume 11/2.

The reduction of the Schiff's bases to give the compounds of the formula (Ib) according to the invention is carried out by customary methods, either by hydrogen in inert organic solvents, such as alcohols, ethers or halogenohydrocarbons, with catalysts, such as Raney nickel, palladium, palladium-on-animal charcoal or platinum, or with hydrides in inert organic solvents, if appropriate in the presence of a catalyst.

The reaction is preferably carried out with hydrides, such as complex alkali metal borohydrides or aluminium hydrides. Sodium borohydride, lithium aluminium hydride or cyanoborohydride are preferably employed here.

Suitable solvents here are all the inert organic solvents which do not change under the reaction conditions. These include, preferably, alcohols, such as methanol, ethanol, propanol or isopropanol, ethers, such as diethyl ether, dioxane or tetrahydrofuran, or dimethylformamide.

Acids are in general used as catalysts. These include, preferably, inorganic acids, such as hydrochloric acid or sulphuric acid, or organic acids, such as carboxylic acids or sulphonic acids, for example acetic acid, trifluoroacetic acid or methane-, ethane-, benzene- or toluene-sulphonic acid.

C) The compounds of the general formula (Ic) according to the invention

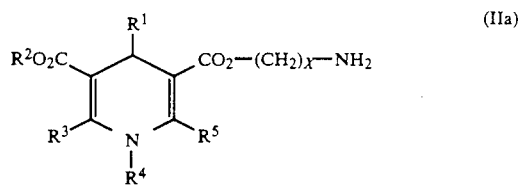

in which
$R^1$–$R^5$ and X have the meaning given,
are reacted with halogen compounds of the formula (IIIc)

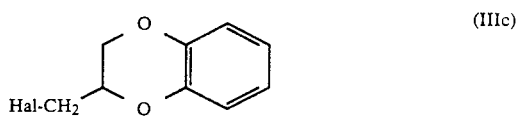

in which
Hal represents fluorine, chlorine, bromine or iodine, preferably chlorine or bromine,
in inert organic solvents, if appropriate in the presence of a base, and, if appropriate, the physiologically acceptable salts are prepared with acids, or by a process in which

[2] Amino-dihydropyridines of the formula (IIa) are reacted with carbonyl compounds of the formula (IIIcc)

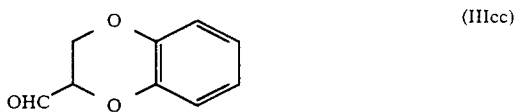

in an inert solvent, if appropriate in the presence of a catalyst, the Schiff's bases thus obtained are reduced in

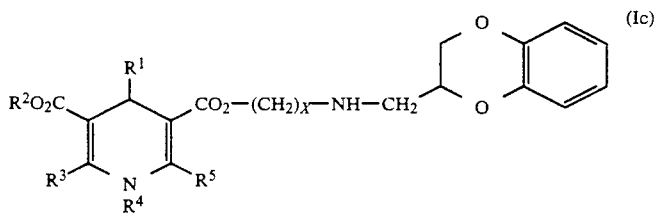

in which
$R^1$–$R^5$ and X have the meaning given,
are obtained by a process in which
[1] Amino-dihydropyridines of the general formula (IIa)

inert solvents in a second step and, if appropriate, the physiologically acceptable salts are then prepared with acids.

Depending on the nature of the starting substances used, processes C1 and C2 can be illustrated by the following equation:

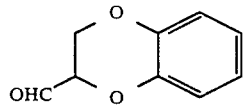  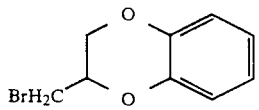

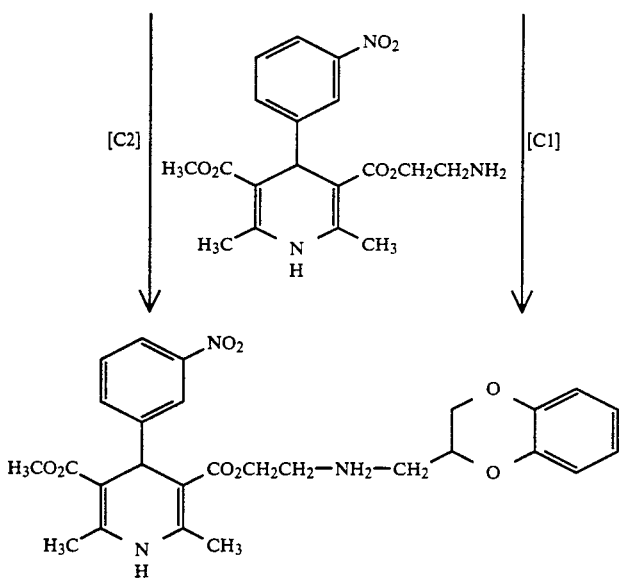

The amino-dihydropyridines (IIa) employed as starting substances are known or can be prepared by known methods [U.S. Pat. No. 3,985,758; European Patent 151,006].

The halogen compounds (IIIc) employed as starting substances are known or can be prepared by known methods [DE-OS (German Published Specification) 3,124,366].

The carbonyl compound of the formula (IIIcc) employed as the starting substance is known [Petragnani et al., Il Farmaco -Ed.Sc.-vol.32-fasc. 7,512].

Suitable solvents for process C1 are the customary organic solvents which do not change under the reaction conditions. These include, preferably, alcohols, such as methanol, ethanol, propanol and isopropanol, ethers, such as diethyl ether, dioxane or tetrahydrofuran, dimethylformamide, dimethylsulphoxide, acetonitrile, ethyl acetate, hexamethylphosphoric acid triamide, pyridine, picoline, N-methylpiperidine or hydrocarbons, such as benzene, toluene or xylene. It is also possible to employ mixtures of the solvents mentioned.

Suitable bases for process C1 are the customary inorganic or organic bases. These include, preferably, alkali metal hydroxides, such as sodium hydroxide or potassium hydroxide, alkali metal carbonates, such as sodium carbonate or potassium carbonate, alkali metal alcoholates, such as sodium methanolate or potassium methanolate, sodium ethanolate or potassium ethanolate or potassium tert.-butanolate, or organic amines, such as trialkylamines, for example triethylamine, pyridine, picoline or N-methylpiperidine, or amides, such as sodium amide or lithium diisopropylamide, or metal-organyls, such as, for example, butyl-lithium or phenyl-lithium.

The reaction is in general carried out in a temperature range from 0° C. to 200° C., preferably from room temperature up to the boiling point of the particular solvent.

The reaction is in general carried out under normal pressure. However, it is also possible to carry out the reaction under increased or reduced pressure.

In general 0.5 to 5 mol, preferably 1 to 2 mol, of halogen compound (IIIc) and 1 to 100, preferably 1 to 50, mol of base are employed in the reaction per mol of amino compound (IIa).

The preparation of the Schiff's bases in the first step of process C2 is carried out in a manner which is known per se in inert organic solvents, if appropriate in the presence of a catalyst and if appropriate in the presence of a water-binding agent. The process according to the invention can be carried out in two steps, that is to say with isolation of the Schiff's bases. It is also possible to carry out the reduction as a one-pot process.

Suitable diluents here are the customary organic solvents which are not changed under the reaction conditions. These include, preferably, alcohols, such as methanol, ethanol, propanol or isopropanol, ethers, such as diethyl ether, dioxane or tetrahydrofuran, halogenohydrocarbons, such as, for example, methylene chloride, chloroform or carbon tetrachloride, dimethylformamide or aromatic hydrocarbons, such as, for example, benzene, toluene or xylene. It is also possible to use mixtures of the solvents mentioned.

Acids are in general used as catalysts. These include, preferably, inorganic acids, such as, for example, hydrochloric acid or sulphuric acid, or organic acids, such as, for example, methane-, ethane-, benzene- or toluenesulphonic acid, or acetic acid. It is also possible to use acetic acid as a mixture with acetic anhydride as a dehydrating agent. The water formed during the reaction can be removed, if appropriate as a mixture with the solvent used, during or after the reaction, for example by distillation, or by addition of water-binding agents, such as, for example, phosphorus pentoxide, or preferably by a molecular sieve.

The reaction is in general carried out at a temperature in the range from 0° C. to 150° C., preferably from 20° C. up to the boiling point of the particular solvent.

The reaction can be carried out under normal, increased or reduced pressure. It is in general carried out under normal pressure.

In carrying out the reaction, the starting substances are in general employed in a molar ratio of carbonyl compound (IIIcc) to amine (IIa) of 0.5:2 to 1:2. Molar amounts of the reactants are preferably used.

The procedure for the preparation of the Schiff's bases from the carbonyl compound (IIIcc) and amines (IIa) is not restricted to the variants described, but can also be carried out by other known methods, which are described, for example, in Houben-Weyt "Methoden der organischen Chemie" ("Methods of Organic Chemistry"), Volume 11/2.

The reduction of the Schiff's bases to give the compounds of the formula (Ic) according to the invention is carried out by customary methods, either by hydrogen in inert organic solvents, such as alcohols, ethers or halogenohydrocarbons, with catalysts, such as Raney nickel, palladium, palladium-on-animal charcoal or platinum, or with hydrides in inert organic solvents, if appropriate in the presence of a catalyst.

The reaction is preferably carried out with hydrides, such as complex alkali metal borohydrides or aluminium hydrides. Sodium borohydride, lithium aluminium hydride or cyanoborohydride are preferably employed here.

Suitable solvents here are all the inert organic solvents which do not change under the reaction conditions. These include, preferably, alcohols, such as methanol, ethanol, propanol or isopropanol, ethers, such as diethyl ether, dioxane or tetrahydrofuran, or dimethylformamide.

Acids are in general used as catalysts. These include, preferably, inorganic acids, such as hydrochloric acid or sulphuric acid, or organic acids, such as carboxylic acids or sulphonic acids, for example acetic acid, trifluoroacetic acid or methane-, ethane-, benzene- or toluenesulphonic acid.

D) The compounds of the general formula (Id) according to the invention

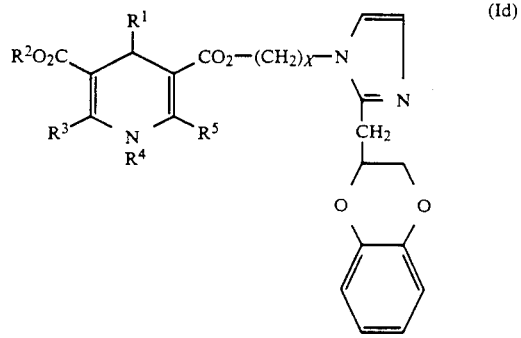

in which
R$^1$-R$^5$ and X have the meaning given, are obtained by a process in which dihydropyridine halogenoesters of the general formula (IId)

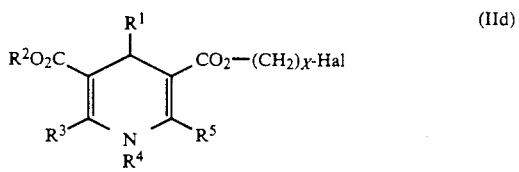

in which
R$^1$-R$^5$ and X have the meaning given and
Hal represents fluorine, chlorine, bromine or iodine, preferably chlorine or bromine,
are reacted with the imidazole of the formula (IIId)

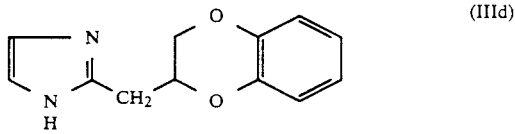

in inert organic solvents, if appropriate in the presence of a base.

The preparation of the compounds of the formula (Id) according to the invention can be illustrated by the following equation:

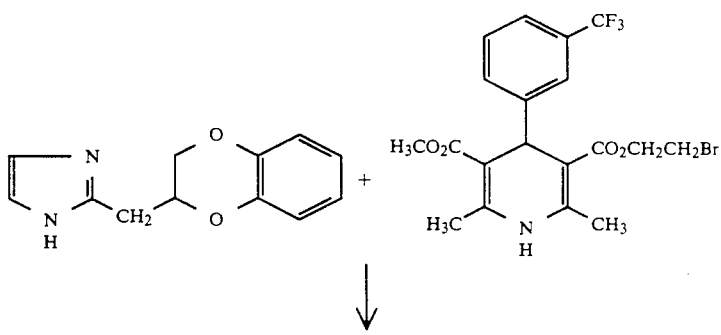

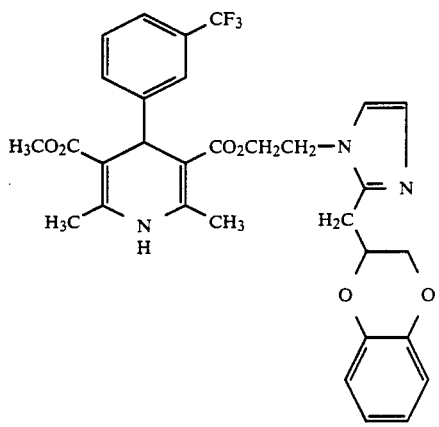

The dihydropyridine halogeno-esters (IId) employed as starting substances are known or can be prepared by known methods [Kuthan et al., Ind. Eng. Chem. Prod. Res. Der. 21, 191 (1982)].

The imidazole (IIId) employed as the starting substance is known or can be prepared by known methods [U.S. Pat. No. 4,302,469].

Suitable solvents are the customary organic solvents which do not change under the reaction conditions. These include, preferably, ethers, such as diethyl ether, dioxane, tetrahydrofuran or glycol mono- or dimethyl ether, amides, such as dimethylformamide or hexamethylphosphoric acid triamide, halogenohydrocarbons, such as methylene chloride, chloroform or carbon tetrachloride, hydrocarbons, such as benzene, toluene or xylene, alcohols, such as methanol, ethanol, propanol or isopropanol, or bases, such as pyridine, picoline, or N-methylpiperidine. Mixtures of the solvents mentioned can also be used.

Suitable bases are the customary inorganic or organic bases, such as sodium or potassium, alkali metal hydrides, such as sodium hydride or potassium hydride, alkali metal amides, such as sodium amide or lithium diisopropylamide, organolithium compounds, such as butyllithium or phenyl-lithium, alkali metal alcoholates, such as potassium methanolate or ethanolate, sodium methanolate or ethanolate or potassium tert.-butanolate, alkali metal hydroxides, such as sodium hydroxide or potassium hydroxide, or alkali metal carbonates, such as sodium carbonate or potassium carbonate, or organic amines, such as trialkylamines, for example triethylamine, pyridine, 1,5-diazabicyclo(4,3,0)non-5-ene or 1,5-diazabicyclo(5,4,0)-undec-5-ene.

The reaction is in general carried out in a temperature range from −20° to 100° C., preferably from 0° C. to 80° C. The reaction can be carried out under normal pressure, but also under increased or reduced pressure. It is in general carried out under normal pressure.

In carrying out the reaction, in general 0.5 to 5 mol, preferably 1 to 1.5 mol, of dihydropyridine halogeno-ester (IId) and 1 to 50, preferably 1 to 10, mol of base are employed per mol of imidazole (IIId).

The compounds according to the invention are suitable as therapeutics for the treatment of ischaemic heart disease and essential hypertension.

In the therapy of ischaemic heart diseases (various clinical forms of angina pectoris, cardiac infarction and cardiac failure), they have a positive influence on the fundamental pathogenetic mechanisms, chiefly the restricted availability of oxygen.

In addition to the calcium-antagonistic activity, the compounds according to the invention also exhibit an antagonizing effect on vascular alpha-adrenoreceptors (alpha-blockade). The therapeutic action spectrum of these substances is accordingly supplemented by venous pooling and a myocardial-preserving reduction in the preload. This improves the therapeutic efficacy and enables a larger number of patients to be treated therapeutically.

The compounds according to the invention also exhibit the same positive action in the treatment of hypertension. Due to the additional reduction in the preload on the heart, hypertensive patients with hyperdynamic circulatory regulation, only some of whom can be treated with conventional products, are also successfully treated. The vein-dilating heart-relieving therapy also leads in hypertensive patients to a reduction in cardiac hypertrophy, an improvement in cardiac output in cases of cardiac insufficiency and a reduction in the oxygen requirement of seriously ill hypertensive patients. The therapeutic possibilities for these chronic, widespread circulatory diseases are thus considerably improved.

The specific calcium-antagonistic action of the compounds according to the invention is examined in a test on isolated rabbit vessels (aorta). In this test, contractions of the vascular muscle are caused in vitro by stimulation with KCl or by noradrenaline. KCl causes contractions due to the depolarization-dependent inwards flow of calcium ions.

These contractions are inhibited by calcium-antagonistic drugs as a function of the dose. Noradrenaline causes contractions by stimulation of the vascular alpha-receptors and the resulting release of calcium ions from the intracellular stores. The noradrenaline-induced contractions are not inhibited by specific calcium antagonists. In contrast, antagonists of the alpha-adrenoreceptors inhibit only the noradrenaline-induced contraction.

Surprisingly, the compounds according to the invention inhibit both depolarization (KCl)-induced and noradrenaline-induced contractions of the isolated vascular muscle of rabbits (see Table 1).

The vein volume of an extremity is measured by plethysmography on anaesthetized cats (ketamine). The arterial blood pressure is also recorded at the same time. Calcium-antagonistic DHP derivatives known hitherto reduce the arterial blood pressure and *reduce* the vein volume by reflectory vein constriction. Antagonists of adrenergic alpha-receptors, such as phentolamine, prazosin or yohimbine, lead to an increase in the vein volume by reduction of the adrenergic venous tone.

The compounds according to the invention reduce the arterial blood pressure and simultaneously *increase* the vein volume, and thereby cause venous pooling in addition to arterial vasodilation (see Table 2).

The compounds according to the invention are also active after oral administration. The arterial blood pressure of conscious rats with hypertension of genetic origin ("spontaneously hypertensive rats" of the Okamoto strain) is measured bloodlessly with a "tail cuff" at defined intervals of time after administration of the substance. The substances to be tested are suspended in a Tylose suspension and administered intragastrally ("orally") in various doses by means of a stomach tube. The compounds according to the invention reduce the arterial blood pressure of hypertensive rats in a clinically relevant dosage (see Table 3).

TABLE 1

Active compound concentration at which the contraction of the aortic ring is inhibited by 50% ($IC_{50}$)
Isolated aortic ring from rabbits, stimulated
a) by KCl depolarization or
b) by noradrenaline

| Example No. | $IC_{50}$ a | $IC_{50}$ b |
| --- | --- | --- |
| 1 | 0.23 mg/l | >10 mg/l |
| 2 | 0.9 mg/l | 3.0 mg/l |
| 3 | 0.23 mg/l | >10 mg/l |
| 4 | 0.4 mg/l | 5.0 mg/l |
| 6 | 0.26 mg/l | 0.36 mg/l |
| 7 | 0.5 mg/l | 1.4 mg/l |
| 8 | 0.3 mg/l | 1.6 mg/l |
| 11 | 0.23 mg/l | 0.18 mg/l |
| 12 | 0.016 mg/l | 0.4 mg/l |
| 13 | 0.08 mg/l | 0.7 mg/l |

TABLE 2

Significant increase in vein capacity in anaesthetized cats in comparison with the reference active substance sodium nitroprusside.

| Example No. | Dose [mg/kg i.v.] |
| --- | --- |
| 9 | 1.0 |
| 11 | 0.1 |
| 12 | 0.1 |

TABLE 3

Reduction in blood pressure in hypertensive rats by 20 mm Hg ($ED_{20}$)

| Example No. | $ED_{20}$ [mg/kg perorally] |
| --- | --- |
| 6 | 1.0 |
| 7 | 31.5 |
| 8 | 31.5 |
| 11 | 3.0 |
| 13 | 3.0 |

The new active compounds can be converted in a known manner into the customary formulations, such as tablets, caoted tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the dosage range stated.

The formulations are prepared, for example, by extending the active compounds with solvents and/or excipients, if appropriate using emulsifying agents and/or dispersing agents, and, for example, in the case where water is used as the diluent, organic solvents can also be used as auxiliary solvents, if appropriate.

Examples of auxiliaries which may be mentioned are: water, non-toxic organic solvents, such as paraffins (for example petroleum fractions), vegetable oils (for example groundnut/sesame oil) and alcohols (for example: ethyl alcohol and glycerol), excipients, such as, for example, natural rock powders (for example kaolins, atuminas, talc and chalk), synthetic rock powders (for example highly disperse silicic acid and silicates) and sugars (for example sucrose, lactose and glucose), emulsifying agents (for example polyoxyethylene fatty acid esters, polyoxyethylene fatty alcohol ethers, alkyl sulphonates, aryl sulphonates), disperging agents (for example ligninsulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various adjuvants, such as starch, preferably potato starch, gelatine and the like. Lubricants, such as magnesium stearate, sodium lauryl sulphate and talc, can furthermore be co-used for tablet-making. In the case of aqueous suspensions, various flavour-improving agents or dyestuffs can be added to the active compounds, in addition to the abovementioned auxiliaries.

In the case of parenteral use, solutions of the active compounds can be employed, using suitable liquid excipients.

In general, it has proved advantageous, in the case of intraveous administration, to administer amounts of about 0.001 to 1 mg/kg, preferably about 0.01 to 0.5 mg/kg of body weight, to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight of the experimental animal or of the mode of administration, but also on the basis of the animal species and its individual reaction to the medicament or the nature of its formulation and the time or interval at which administration takes place. Thus it can in some cases suffice to manage with less than the abovementioned minimum amount, whilst in other cases the upper limit mentioned must be exceeded. Where relatively large amounts are administered, it may be advisable to divide these into several individual doses over the course of the day. The same dosage range is envisaged for administration in human medicine. The above statements also apply here in the general sense.

Unless expressly indicated otherwise, the $R_f$-values of the following examples were determined using thin layer chromatography precoated plates, silica gel 60 $F_{254}$ from E. Merck, Darmstadt.

EXAMPLE 1

3-Methyl
5-{6-[2-[N-benzyl-N-(2-phenoxy-1-methylethyl)-aminoethylamino]hexyl}
1,4-dihydro-2,6-dimethyl-4-(3-nitrophenyl)-pyridine-3,5-dicarboxylate

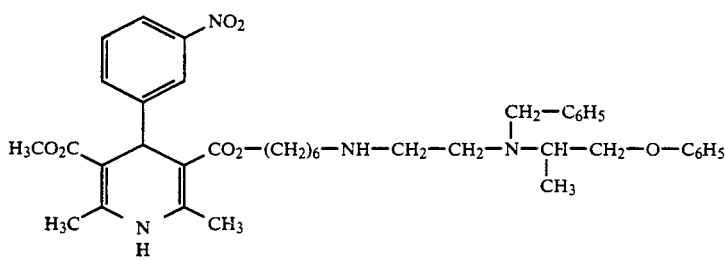

1.5 g (0.0035 mol) of 3-methyl 5-(6-aminohexyl) 1,4-dihydro-2,6-dimethyl-4-(3-nitrophenyl)pyridine-3,5-dicarboxylate are boiled under reflux with 1.1 g (0.0035 mol) of N-benzyl-N-phenoxyisopropyl-$\beta$-chloroethylamine and 1.2 g of potassium carbonate in 60 ml of analytical grade dioxane for 20 hours. The reaction mixture is cooled and concentrated on a rotary evaporator and the residue is purified on a silica gel column (chloroform:methanol/10:1). The cooled oil is dried under a high vacuum. Fractionation gives a 540 mg yield (23% of theory) as an amorphous powder.

$R_f$: 0.18 (10:1/CHCl$_3$:CH$_3$OH).

EXAMPLE 2

3-Methyl
5-{6-[bis-[2-[N-benzyl-N-(2-phenoxy-1-methylethyl)aminoethyl]aminoethyl]aminohexyl]}
1,4-dihydro-2,6-dimethyl-4-(3-nitrophenyl)-pyridine-3,5-dicarboxylate

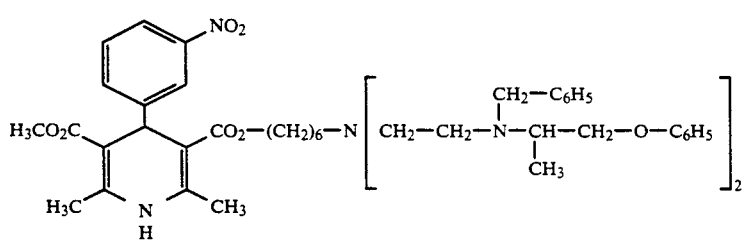

From the reaction mixture obtained in the preparation of Example 1, 490 mg of the compound of Example 2 are obtained in the form of an amorphous powder during fractionation.

$R_f$: 0.42 (10:1/CHCl$_3$:CH$_3$OH).

EXAMPLE 3

3-Isopropyl
5-{2-[2-[N-benzyl-N-(2-phenoxy-1-methylethyl)-aminoethylamino]ethyl}
1,4-dihydro-2,6-dimethyl-4-(3-nitrophenyl)pyridine-3,5-dicarboxylate

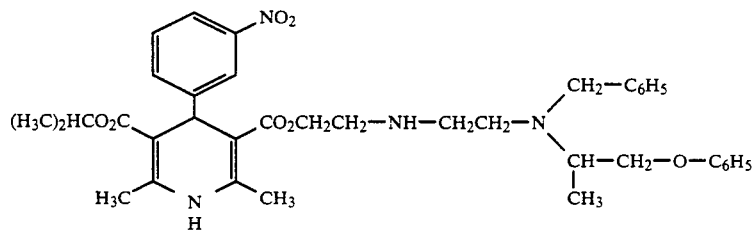

Yield: 27% of theory.
Melting point: amorphous.
$R_f$: 0.42 (10:1/CHCl$_3$:CH$_3$OH).

EXAMPLE 4

3-Isopropyl 5-{2-[bis-[2-[N-benzyl-N-(2-phenoxy-1-methylethyl)amino]ethyl]amino]ethyl} 1,4-dihydro-2,6-dimethyl-4-(3-nitrophenyl)-pyridine-3,5-dicarboxylate

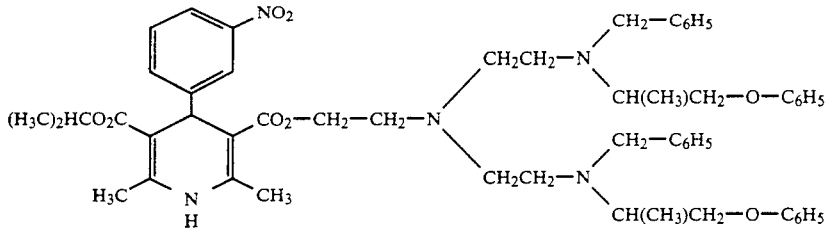

Yield: 26% of theory.
Melting point: amorphous.
$R_f$: 0.8 (10:1/CHCl$_3$:CH$_3$OH).

EXAMPLE 5

3-Methyl 5-[6-(1,3,4,6,7,11b-hexahydro-8,9-dimethoxy-2H-benzo[a]quinolizin-2-yl-amino)hexyl] 1,4-dihydro-2,6-dimethyl-4-(3-nitrophenyl)pyridine-3,5-dicarboxylate

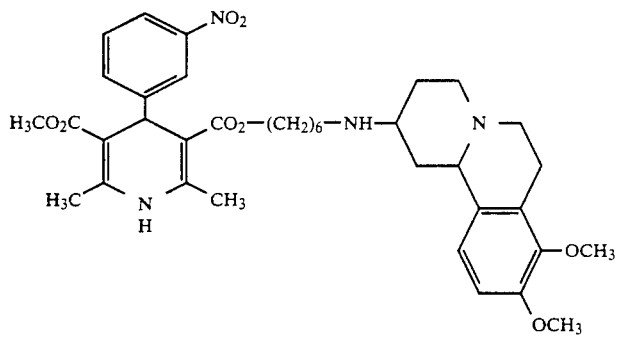

1.3 g (0.005 mol) of 1,3,4,6,7,11b-hexahydro-8,9-dimethoxy-benzo[a]quinolizin-2-one are dissolved in 30 ml of methanol and the pH is brought to 6 with methanolic hydrochloric acid. 2.1 g (0.005 mol) of 3-methyl 5-(6-aminohexyl 1,4-dihydro-2,6-dimethyl-4-(3-nitrophenyl)-pyridine-3,5-dicarboxylate in methanol are added to this solution and the mixture is stirred with a 3 Å molecular sieve at room temperature for 2.5 hours. 320 mg of sodium cyanoborohydride are then added in portions and the mixture is stirred at room temperature for 20 hours. The reaction mixture is filtered and the filtrate is acidified and concentrated on a rotary evaporator. Methylene chloride is added to the residue, the mixture is rendered alkaline with dilute sodium hydroxide solution and the organic phase is washed with water, dried over sodium sulphate, filtered and concentrated in vacuo. The residue is purified on a silica gel column (chloroform: methanol: triethylamine/10:0.5:0.25). The product thus obtained is then dried under a high vacuum.

Yield: 1.6 g (48% of theory), amorphous.
$R_f$: 0.76 (1:1/CHCl$_3$:CH$_3$OH).

The following compounds are prepared analogously to Example 5:

EXAMPLE 6

3-Methyl 5-[2-(1,3,4,6,7,11b-hexahydro-8,9-dimethoxy-2H-benzo[a]quinolizin-2-yl-amino)ethyl] 1,4-dihydro-2,6-dimethyl-4-(3-nitrophenyl)pyridine-3,5-dicarboxylate

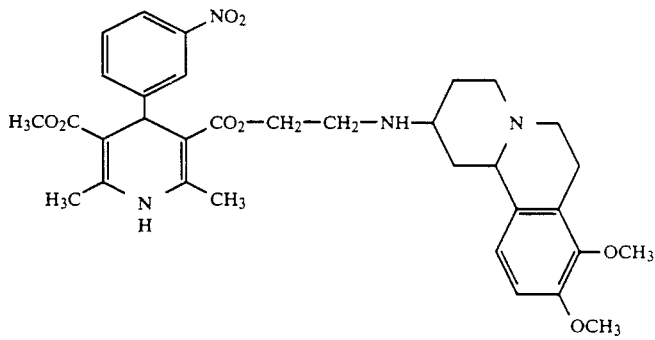

Yield: 48% of theory.
Melting point: amorphous.
$R_f$: 0.3 (20:1:0.5/CHCl$_3$:CH$_3$OH:(C$_2$H$_5$)$_3$N).

EXAMPLE 7

3-Isopropyl
5-[3-(1,3,4,6,7,11b-hexahydro-8,9-dimethoxy-2H-benzo[a]quinolizin-2-yl-amino)propyl]
1,4-dihydro-2,6-dimethyl-4-(3-nitrophenyl)pyridine-3,5-dicarboxylate

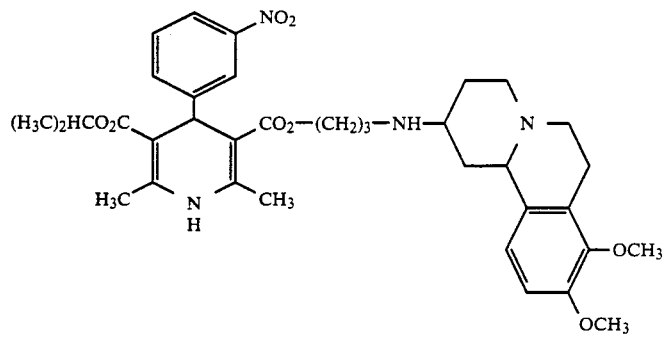

Yield: 47% of theory.
Melting point: amorphous.
R$_f$: 0.76(1:1/CHCl$_3$:CH$_3$OH).

EXAMPLE 8

3-Isopropyl
5-[2-(1,3,4,6,7,11b-hexahydro-8,9-dimethoxy-2H-benzo[a]quinolizin-2-yl-amino)ethyl]
1,4-dihydro-2,6-dimethyl-4-(3-nitrophenyl)pyridine-3,5-dicarboxylate Yield: 47% of theory.
Melting point: amorphous.
R$_f$: 0.33 (20:1:0.5/CHCl$_3$:CH$_3$OH:(C$_2$H$_5$)$_3$N).

EXAMPLE 9

3-Isopropyl
5-[2-(1,3,4,6,7,11b-hexahydro-9-methoxy-2H-benzo[a]quinolizin-2-yl)amino]ethyl
1,4-dihydro-2,6-dimethyl-4-(3-nitrophenyl)pyridine-3,5-dicarboxylate Yield: 27.1% of theory.
R$_f$: 0.14 (CHCl$_3$:CH$_3$OH:NH$_3$/20:1:0.05).

EXAMPLE 10

3-Methyl 5-[6-(benzodioxan-2-yl-methylamino)hexyl] 1,4-dihydro-2,6-dimethyl-4-(3-nitrophenyl)pyridine-3,5-dicarboxylate

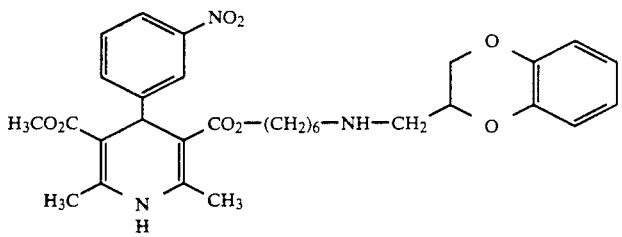

Process A 430 mg (0.001 mol) of 3-methyl 5-(6-aminohexyl) 1,4-dihydro-2,6-dimethyl-4-(3-nitrophenyl)pyridine-3,5-dicarboxylate are boiled under reflux with 230 mg (0.001 mol) of 2-bromomethyl-1,4-benzodioxane and 200 mg of $K_2CO_3$ in 30 ml of analytical grade dioxane for 15 hours. The reaction mixture is cooled and concentrated on a rotary evaporator. Sodium bicarbonate solution is added to the residue and the mixture is extracted twice with 50 ml of methylene chloride each time. The combined organic phases are dried over sodium sulphate, filtered and concentrated in vacuo. The residue is purified on a silica gel column (ethyl acetate: methanol/4:1). The product thus obtained is then dried under a high vacuum.

Yield: 310 mg (53% of theory).
Melting point: amorphous.
$R_f$: 0.43 (4:1/ethyl acetate: $CH_3OH$).

Process B 82 mg (0.0005 mol) of 2-formyl-1,4-benzodioxane are dissolved in 3 ml of methanol and the pH is brought to 6 with methanolic hydrochloric acid. A solution of 200 mg (0.005 mol) of 3-methyl 5-(6-aminohexyl)1,4-dihydro-2,6-dimethyl-4-(3-nitrophenyl)pyridine-3,5-dicarboxylate and 10 ml of methanol is added and the reaction mixture is stirred with a 3 Å molecular sieve at room temperature for 2.5 hours. 32 mg of sodium cyanoborohydride are then added in portions and the mixture is stirred for 20 hours. After filtration and concentration on a rotary evaporator, water and methylene chloride are added to the residue. The organic phase is separated off, dried with sodium sulphate and concentrated. The residue is purified over a silica gel column (ethyl acetate). The product thus obtained is dried under a high vacuum.

Yield: 158 mg (57% of theory).
Melting point: amorphous.
$R_f$: 0.49 (4:1/ethyl acetate: $CH_3OH$).

The following compounds are prepared analogously to Example 10:

EXAMPLE 11

3-Methyl 5-{2-[N-(1,4-benzodioxan-2-yl-methyl)-N-methylamino]ethyl} 1,4-dihydro-2,6-dimethyl-4-(3-nitrophenyl)-pyridine-3,5-dicarboxylate

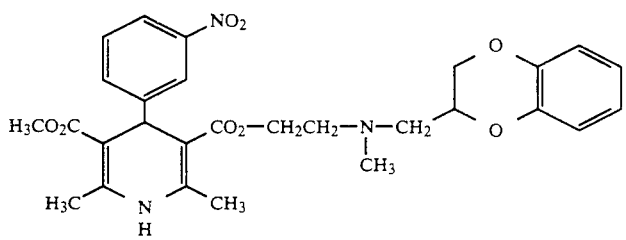

Melting point: amorphous.
Yield: 21% of theory.
$R_f$: 0.72 (ethyl acetate).

EXAMPLE 12

3-Isopropyl 5-[2-(1,4-benzodioxan-2-yl-methylamino)ethyl] 1,4-dihydro-2,6-dimethyl-4-(3-nitrophenyl)pyridine-3,5-dicarboxylate

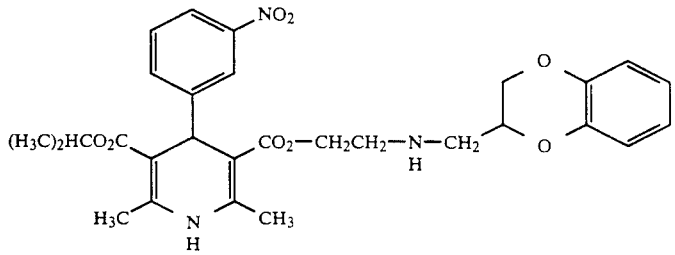

Melting point: amorphous.
Yield: 45% of theory.

R$_f$: 0.41 (ethyl acetate).

EXAMPLE 13

3-Methyl 5-[2-(1,4-benzodioxan-2-yl-methylamino)ethyl] 1,4-dihydro-2,6-dimethyl-4-(3-nitrophenyl)pyridine-3,5-dicarboxylate

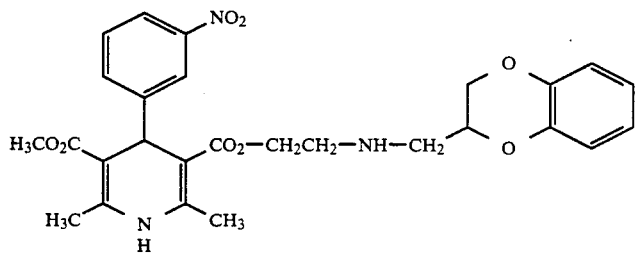

Yield: 64% of theory.
Melting point: amorphous.
R$_f$: 0.33 (ethyl acetate).

EXAMPLE 14

3-Isopropyl-5-[3-(1,4-benzodioxan-2-yl-methylamino)-propyl] 1,4-dihydro-2,6-dimethyl-4-(3-nitrophenyl)pyridine-3,5-dicarboxylate

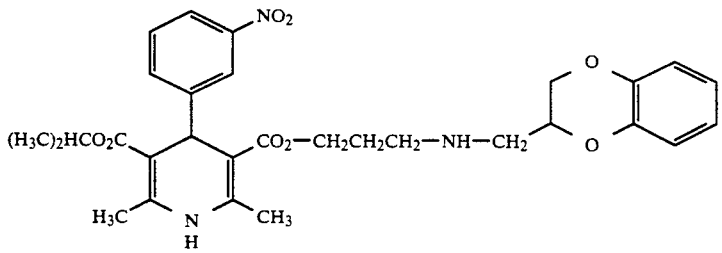

Yield: 34% of theory.
Melting point: amorphous.
R$_f$: 0.72 (4:1/ethyl acetate: CH$_3$OH).

EXAMPLE 15

3-Methyl 5-{2-(1,4-benzodioxan-2-yl-methyl)imidazol-1-yl]ethyl} 1,4-dihydro-2,6-dimethyl-4-(3-nitrophenyl)pyridine-3,5-dicarboxylate

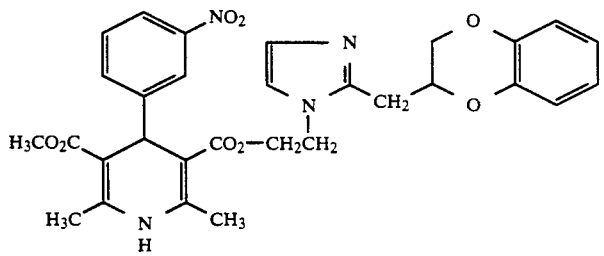

180 mg (0.006 mol) of sodium hydroxide and 15 ml of analytical grade dimethylformamide are cooled to 0° C. under nitrogen and 620 mg (0.0025 mol) are added. The mixture is stirred at room temperature for 0.5 hour and a solution of 1.1 g (0.0025 mol) of 3-methyl 5-(2-bromoethyl) 1,4-dihydro-2,6-dimethyl-4-(3-nitrophenyl)pyridine-3,5-dicarboxylate and 20 ml of analytical grade dimethylformamide is then added dropwise at 0° C. After a further 30 minutes at room temperature, H$_2$O is added dropwise to the reaction mixture, with cooling, and the mixture is extracted 3 times with ethyl acetate. The combined organic phases are washed 3 times with H$_2$O, dried over sodium sulphate and concentrated on a Rotavapor. The residue is purified over a silica gel column (ethyl acetate). The product thus obtained is dried under a high vacuum.
Yield: 33% of theory.
Melting point: amorphous.
R$_f$: 0.15 (ethyl acetate).

The following compounds are prepared analogously to Example 15:

EXAMPLE 16

3-Methyl 5-{6-[2-(1,4-benzodioxan-2-yl-methyl)imidazol-1-yl]hexyl} 1,4-dihydro-2,6-dimethyl-4-(3-nitrophenyl)pyridine-3,5-dicarboxylate

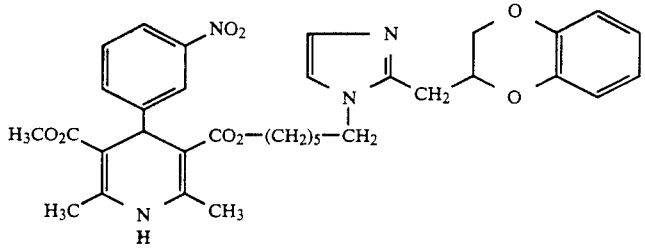

Yield: 42% of theory.
Melting point: amorphous.
$R_f$: 0.15 (ethyl acetate).

EXAMPLE 17

3-Methyl-5-{6-[2-(1,4-benzodioxan-2-yl-methyl)imidazol-1-yl]hexyl} 1,4-dihydro-2,6-dimethyl-4-(2-trifluoromethylphenyl)-pyridine-3,5-dicarboxylate

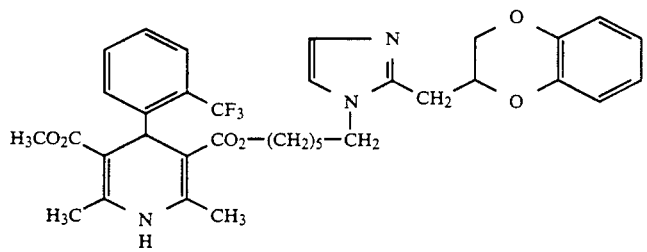

Yield: 46% of theory.
Melting point: amorphous.
$R_f$: 0.16 (ethyl acetate).

We claim:

1. An aminoalkyl ester of a dihydropyridinedicarboxylic acid of the formula

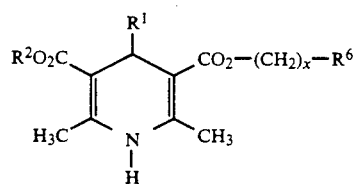

in which $R^1$ is phenyl, the phenyl ring being optionally substituted by 1 or 2 identical or different substituents from the group consisting of chlorine, trifluoromethyl, nitro and cyano, $R^2$ is a straight-chain or branched hydrocarbon radical which has up to 7 carbon atoms and is optionally interrupted in the chain by an oxygen atom and said hydrocarbon radical is optionally substituted by fluorine and cyano, X is a number from 2 to 6, and $R^6$ represents a radical of the formula

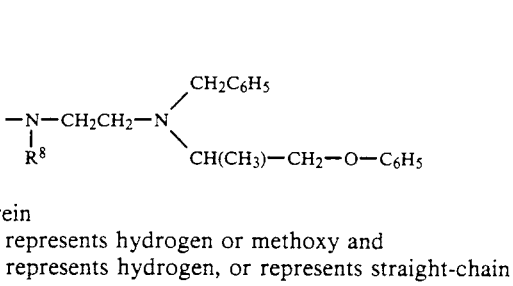

wherein $R^7$ represents hydrogen or methoxy and $R^8$ represents hydrogen, or represents straight-chain or branched $C_1-C_6$-alkyl, or represents the group of the formula

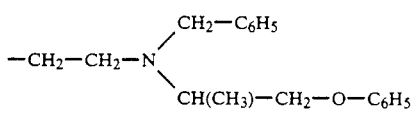

or a physiologically acceptable salt thereof.

2. A circulation-active composition comprising a circulation-active effective amount of a compound or salt according to claim 1 and a physiologically acceptable diluent.

3. A unit dose of a composition according to claim 2 in the form of a tablet, capsule or ampule.

4. A method of improving the circulation of a patient in need thereof which comprises administering to such patient a circulation-active effective amount of a compound or salt according to claim 2.

* * * * *